(12) United States Patent
Arkush

(10) Patent No.: US 9,452,317 B2
(45) Date of Patent: Sep. 27, 2016

(54) BREATHING AND RESPIRATORY MUSCLE TRAINING METHOD AND SYSTEM

(71) Applicant: Bezalel Arkush, Weehawken, NJ (US)

(72) Inventor: Bezalel Arkush, Weehawken, NJ (US)

(*) Notice: Subject to any disclaimer, the term of this patent is extended or adjusted under 35 U.S.C. 154(b) by 0 days.

(21) Appl. No.: 14/433,222

(22) PCT Filed: Oct. 11, 2013

(86) PCT No.: PCT/US2013/064725
§ 371 (c)(1),
(2) Date: Apr. 2, 2015

(87) PCT Pub. No.: WO2014/059389
PCT Pub. Date: Apr. 17, 2014

(65) Prior Publication Data
US 2015/0258370 A1 Sep. 17, 2015

Related U.S. Application Data

(60) Provisional application No. 61/712,515, filed on Oct. 11, 2012.

(51) Int. Cl.
*A63B 24/00* (2006.01)
*A63B 23/18* (2006.01)
(Continued)

(52) U.S. Cl.
CPC ............. *A63B 23/18* (2013.01); *A61B 5/087* (2013.01); *A61B 5/486* (2013.01); *A63B 24/0062* (2013.01); *A63B 71/0622* (2013.01); *A63F 13/20* (2014.09); *G09B 19/003* (2013.01); *A63B 2024/0065* (2013.01); *A63B 2024/0068* (2013.01); *A63B 2024/0078* (2013.01); *A63B 2024/0093* (2013.01);
(Continued)

(58) Field of Classification Search
CPC .. A61B 5/0833; A61B 5/083; A61B 5/0215; A61B 5/0876; A63B 23/18; A63B 2230/405; A63B 2230/505; A63B 71/0622; A63B 24/00; A63B 24/0062; A63B 2024/0065; A63B 2024/0068; A63B 2024/0078; A63B 2024/0096; A63B 2071/0655; A63B 2071/0683; A63B 2208/12; A63B 2220/56; A63B 2225/50
See application file for complete search history.

(56) References Cited

U.S. PATENT DOCUMENTS

| | | | | |
|---|---|---|---|---|
| 5,189,240 A * | 2/1993 | Kawashima | ......... | G10H 1/0553 84/724 |
| 7,108,659 B2 * | 9/2006 | Ross | ...................... | A61B 5/083 600/529 |
| 7,754,955 B2 * | 7/2010 | Egan | .................... | G09B 15/023 84/464 R |
| 8,740,750 B2 * | 6/2014 | Jerichow | .............. | A61B 5/0833 455/410 |
| 9,288,840 B2 * | 3/2016 | Park | ...................... | H04W 88/02 |

(Continued)

FOREIGN PATENT DOCUMENTS

EP 1977792 A1 10/2008
RU 198336 U1 10/2010

OTHER PUBLICATIONS

Written Opinion of PCT/US13/064725 Mailed Jan. 23, 2014.

*Primary Examiner* — Glenn Richman
(74) *Attorney, Agent, or Firm* — Robert W. J. Usher

(57) ABSTRACT

A software operated method/system for both breathing training and respiratory muscle training in which a user inhales and exhales via a mouthpiece through a hand-held breathing chamber so that pressure, time and direction of air breathed through the chamber is automatically measured. The breathing results are automatically processed and displaying on a remote screen as a real-time interactive graphic representing such air pressure, time and direction. The users base-line is established and a menu of training choices including interactive games is displayed.

11 Claims, 15 Drawing Sheets

(51) Int. Cl.
    *A61B 5/087* (2006.01)
    *A61B 5/00* (2006.01)
    *A63B 71/06* (2006.01)
    *A63F 13/20* (2014.01)
    *G09B 19/00* (2006.01)

(52) U.S. Cl.
    CPC ........ *A63B 2071/0655* (2013.01); *A63B 2071/0683* (2013.01); *A63B 2208/12* (2013.01); *A63B 2220/56* (2013.01); *A63B 2225/50* (2013.01); *A63B 2230/405* (2013.01); *A63B 2230/505* (2013.01)

(56) References Cited

U.S. PATENT DOCUMENTS

| | | | |
|---|---|---|---|
| 2004/0186390 A1* | 9/2004 | Ross | A61B 5/083 600/532 |
| 2006/0282002 A1* | 12/2006 | Wang | A61B 5/0876 600/538 |
| 2008/0034836 A1* | 2/2008 | Eigler | A61B 5/0215 73/1.61 |
| 2012/0192121 A1* | 7/2012 | Bonnat | G06F 3/0488 715/863 |

* cited by examiner

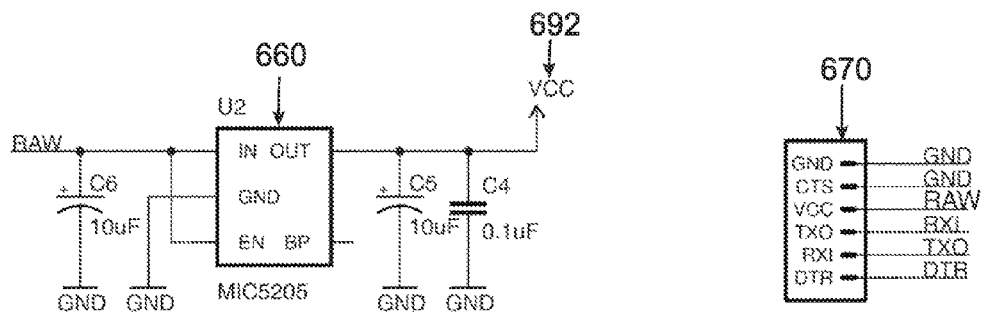
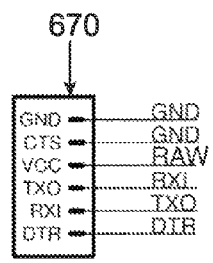
FIG. 6A  FIG. 6B
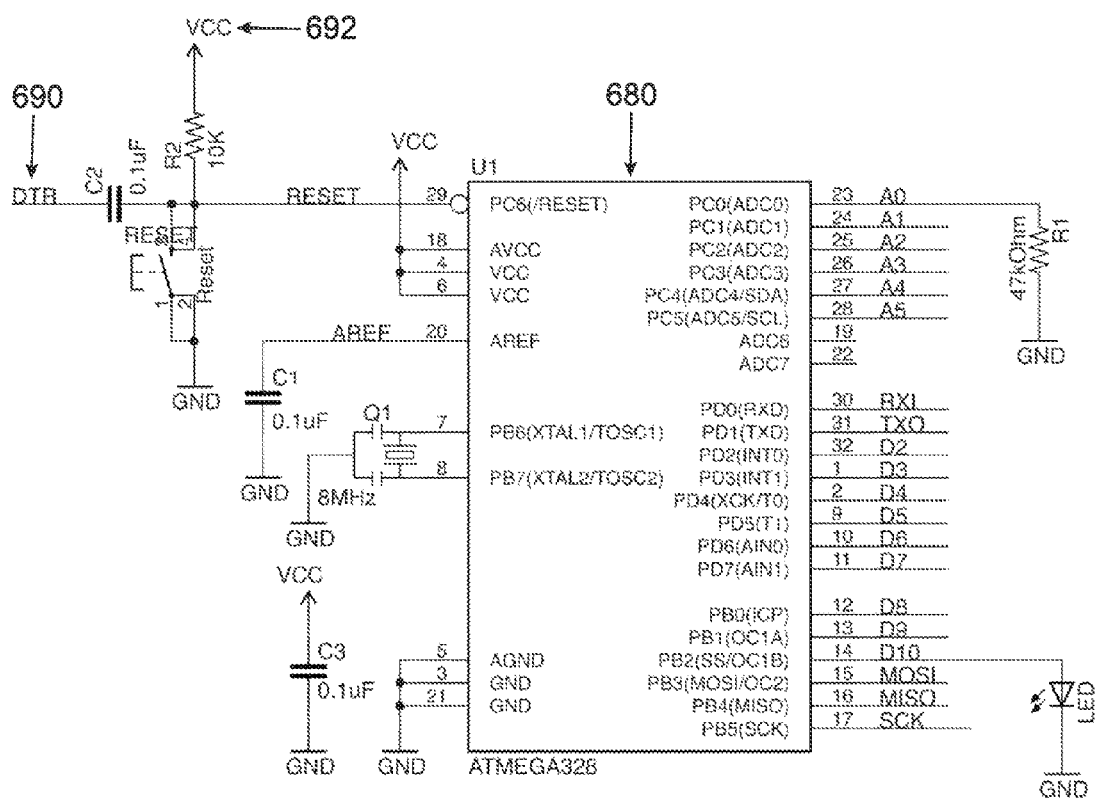
FIG. 6C

EXHALE
Liters per Second
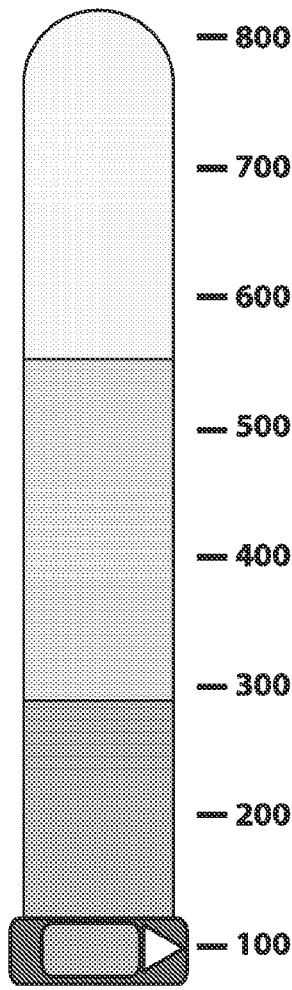
1. Breathe in fully (the lungs must be completely full)
2. Seal the lips and teeth tightly around the mouthpiece and then immediately...
3. BLAST the air out as fast and as long as possible until the lungs are completely empty (10 seconds is optimal).
4. Press redo icon for retesting.
BACK    NEXT
FIG. 9

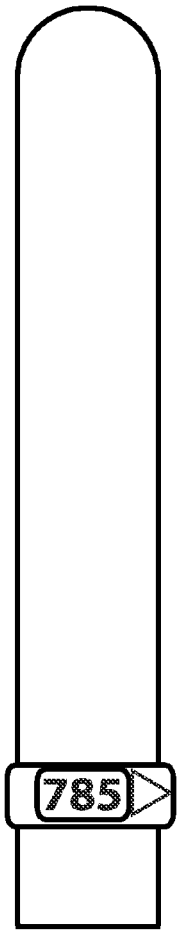

INHALE
mL Inspired Volume

1. Put the mouthpiece in your mouth and close your lips tightly around it. Do not block the mouthpiece with your tongue.
2. Inhale slowly and deeply through the mouthpiece to raise the indicator. Try to make the indicator rise up to the level of the target pointer.
3. When you cannot inhale any longer, remove the mouthpiece and hold your breath for at least 3 seconds.
4. Exhale normally.
5. Press redo icon for retesting.

BACK   NEXT

FIG. 10

BREATHING AND RESPIRATORY MUSCLE TRAINING METHOD AND SYSTEM

RELATED APPLICATION

Priority is claimed from my U.S. provisional application 61/712,515 filed 11 Oct. 2012, the disclosure of which is incorporated herein by reference

FIELD OF THE INVENTION

The present invention relates to respiratory training and, in particular, to a new and improved breathing training and respiratory muscle training system which allows the stress placed upon the pulmonary muscles to be adjusted as required for the training and exercise level of the individual and provides immediate/real-time continuous audio/visual feedback to the user as well as past and present data of the activity.

BACKGROUND OF THE INVENTION

U.S. Pat. No. 8,459,255 teaches a hand-held, muscle training device, the disclosure of which is incorporated herein by reference.

However, in addition to such device there is a need for an integrated, real-time breathing training system which include both breathing training and respiratory muscle training.

SUMMARY OF THE INVENTION

According to one aspect, the invention provides a computer operated method for both breathing training and respiratory muscle training comprising the steps of providing a breathing chamber having a mouthpiece whereby a user can inhale and exhale air through the chamber; automatically measuring pressure, time and direction of air breathed through the chamber; automatically processing and displaying on a remote screen a real-time interactive graphic representing such personal test results of air pressure, time and direction; displaying the test results and, subsequently determining and displaying at least one of a stored series of appropriate personal training routines of different difficulties on the screen in accordance with a test result, for user selection, whereby the user can monitor personal breathing performance on a real time basis and perform personal training routines.

The invention also provides a system for both breathing training and respiratory muscle training comprising a hand-held breathing device and training software; the breathing device comprising a chamber having an air port and a separate mouthpiece whereby a user can inhale and exhale through the chamber; an air pressure sensor in the chamber for providing an electrical signal signifying the direction and pressure of the air breathed through the chamber and, one of cable and wireless means for outputting such signal to a remote computing device or cloud, installed with the software, to automatically process and display a real-time interactive graphic representing such air pressure, time and direction and appropriate personal training routines on a remote screen;

whereby the user can monitor personal breathing performance on a real time basis and perform the training routines.

The capacity of the invention to measure and track respiratory parameters and integrate the measurements of the respiratory profile with the training and therapy sessions, personalizes the training therapy exercises to real-time needs of the user.

The combination of inhale and exhale breathing instruction and feedback at different resistance levels couples with timing of the breathing provides a new control and benefits to the trainer/therapist as well as to the end user.

The system can instruct and measure the timing of an inhale and exhale breath, the time of holding the breath and instruction of when to release the breath and measure when such an activity is with accordance of the designated optimal breathing cycle for the trainer.

The system device can also encourage and monitor rate of breathing and timing for an inhale, exhale and holding breath. Training and monitoring the rate of breathing can help users optimize the rhythm of breathing for athletic purposes as well as relaxation training. Continuous tracking of the respiratory profile of the user over time with the analysis of the training therapy provides an additional insight into the personalization of the therapy and training while seeing improvement or lack of while analyzing the training over time.

Medical application of the device can be used to improve the conditions of the following:
Post operative patients
Pre operative patients
COPD patients
CHF patients
CF patients
Asthma management tool for children and older patients
Respiratory Training for Asthma
Support system for relaxation of Asthma patients
Weaning of chronic ventilator patients
Sport, Fitness and Lifestyle application of the device can be used to improve the conditions of the following:
Sport
Athletics.Runners
Cyclists
Divers
Swimmers
Gym goers
Lifestyle
Stress Management
Pregnant Women
Sleep Improvement
Singers
Wind Instrument players The RespiRight (trade mark) breathing monitoring device is an optimal breathing trainer and exerciser comprising a tubular body having a mouthpiece-accepting end, a restrictor port end and a medial portion there between.

RespiRight system can be operated as a standalone unit or as a device connected to any kind of remote computerized device with a screen including mobile smart phone or tablet, a game platform such as Nintendo or Xbox computer or a gym based system or any other computing device where the interaction instructions and feedback are displayed. (E.g connected to an iPhone/iPad device).

The RespiRight (trade mark) device is also designed as a new type of a computer game controller where the game is controlled by breathing in and out at a different resistance level. Through, different pressures and duration of breathing, one can control the game on any interactive computer based system. It can be used for games designed specifically for the device or adapted to existing games.

Device Electronic Components—
1. Microprocessor
2. Air pressure sensor (IC PRESSURE SENSOR 16.7 PSI 8SSOP MP3H6115AC6U manufactured by Freescale Semiconductor)
3. LED
4. Rotary Dip Switch The user breathes into the housing, creating a pressure reading on the air pressure sensor. The pressure reading is influenced by the user's breathing force and the resistance setting of the device. The resistance setting is known from the rotational position of the rotary dip switch which is rotated by rotation of the restrictor.

The LED, air pressure sensor and the rotary dip switch are connected to the microprocessor/microcontroller which records and processes the outputs/settings.

As the air pressure varies, the air pressure sensor transmits a variable analog resistance reading signal to the microcontroller. The microprocessor interprets the air pressure reading signal and varies the intensity of the LED accordingly while also transmitting the air pressure reading signal over to the mobile device via a Serial Communication cable or Via Bluetooth.

One mode of operation is conducting a test breathing process which tests and records the current inhaling and exhaling capability of the user and stores the information and displays it to the user on a daily, weekly, monthly and yearly progress chart.

The RespiRight offers the entire functionality [full simulation] of existing respiratory therapy devices but with the additional capability to store and compare activities which are geared toward the enhancement of respiratory capabilities such as an Incentive spirometers, deep breathing trainers and respiratory muscle trainers devices.

The training session can be planned by the user, by the respiratory therapist as well as any other healthcare provider or by sport and fitness trainers.

Another mode of operation is to include within the unit a 3-axis accelerometer be able to detect the user's motion while performing the breathing exercises. The 3 Axis Accelerometer provides data of the user posture/position, if he is standing sitting or lying as well as the user's movements.

The information from the training is captured stored and analyzed on the computing device locally or stored and analyzed on a secure cloud server location by sending the information to a secured server location.

The training session can be planned by the user, by the respiratory therapists, the healthcare provider or by the sport trainers.

Interchangeable mouth pieces enable adjustment to the type of training desired as well as the type of trainer. Users will be provided with differently shaped mouth pieces which produce different air flows based on the different structure/shaped mouthpieces. For example, a recommended breathing exercise for Asthma patient is a "pursed lips" training. One of the mouthpieces is relatively narrow so that the user has to purse his lips to grab the mouthpiece. In athlete training there will be a wide opening to let air flow quicker.

The RespiRight device/system can measure the Inhaling activity as well as the exhaling activity of the user and it measures the flow of air over the pressure sensor which is placed inside the unit and the increased pressure differential of both inhaling and exhaling at different resistance levels. The information provided by the measurement initiates the level of training required. The hand-held device has a rotating air flow restrictor/valve comprising an end cap formed with a ring of orifices of successively decreasing sizes which can be manually rotated by the user into successive registration with a single air port in an opposed stationary valve plate covering an open end of the tubular medial housing part to alter the resistance to air flow and thereby enable the user to change the level of difficulty as instructed, by changing the resistance to breathing in and breathing out. The user can choose a difficulty level by turning the rotating restrictor. The restrictor results in a different air flow at each level and thus provides a difference in the resistance level at each rotational position. Each rotation alters the setting of the dip switch located at the center of the restrictor and sends the information to the computing device.

Another option is that the levels can be changed automatically by an input of the training regime and via an electro-mechanical element which will adjust the resistance level of the device for trainers.

An additional option is to restrict air flow by a variable diaphragm or shutter type mechanism such that rotating the cap causes the shutter to become narrower or wider. The change in the shutter diameter creates a different air flow through the tubular body thus registering different pressures.

The hand-held device has an LED light indicating the ON position as well as an indication that it is connected to a mobile or a computer. Blowing into the device causes the LED to dim according to an input from the reading of the pressure sensor. The LED is at maximum brightness when the unit is at rest, when the user is either inhaling or exhaling into the system the microprocessor a numerical count/reading comprising positive numbers (for exhaling) or negative numbers (for inhaling) and sends correspondingly different current levels to the LED which causes it to dim as an indication of the breathing activity, thereby providing an immediate feedback to the user displayed on the device itself.

The system automatically detects the resistance level of the breathing device and can send the mobile device information to ensure that the user does not train at the wrong level and can restrict the training to the right level. Each rotation is recognized by the system since it activated a dip switch unit located at the center of the rotating restrictor, each rotation of the restrictor changes the position of the dip switch and sends this information to the micro controller which calculates the pressure sensor reading for each position of the dip switch.

The system guides the user throughout his activity by pop-up screens as well as providing audiovisual feedback to the user prompting him to take actions.

The system provides a gamification layer which encourages the users to continue training by providing ongoing incentives and showing progress and challenges as well as enabling digital social interaction by connecting other trainees and friends to be part of the training experience. A sample (Diver) game causes a diver to rise and descend The game software resides on the mobile smartphone or tablet, a game platform such as Nintendo or Xbox and gym based system or any other computing based device attached to the hand-held breathing device either by a cable connector or wireless connection with Bluetooth and other wireless protocols.

After the user has registered, if the game is testing the user's breathing capability, the first phase is having the user inhale and exhale 3 times into the hand-held unit. The hand-held unit sends the measurements to an interactive computer with a display and, based on these readings, averages the information and creates a respiratory profile (RP) of this specific user.

Additional user input is provided by the system software/program which enables the user to input on a sliding ruler type on the screen, subjective status of several parameters such as cough, wheeze, and shortness of breath or chest tightness. These indicators can also be a part of the user's respiratory profile.

The game objective is to control the movement of objects in this case a diver image with breathing, and to divert the diver to places that he can collect items and gains as many points as possible by collecting floating treasures such as coins, pearls and archeological artifacts at the bottom of the sea. There are also dangerous creatures which the diver must avoid in order not to end the game abruptly. Another factor is that the diver's tanks are running out of oxygen and he has to plan to resurface and change the oxygen tanks on the surface.

Once the user has finished the first level of resistance to air-flow, avoids all the creatures and collects treasures he advances to the next level by turning the restrictor to provide the next higher level (selecting the adjacent, smaller diameter inlet port). For every activity at the next level the user collects double the points of the previous game level.

The system has a network mode in which a few devices are being used simultaneously in a clinic and gym environment and the therapist/trainer can control and view the performance of every user.

BRIEF INTRODUCTION TO THE DRAWINGS

Embodiments of the invention will now be described with reference to the accompanying drawings in which.

Figure 1:
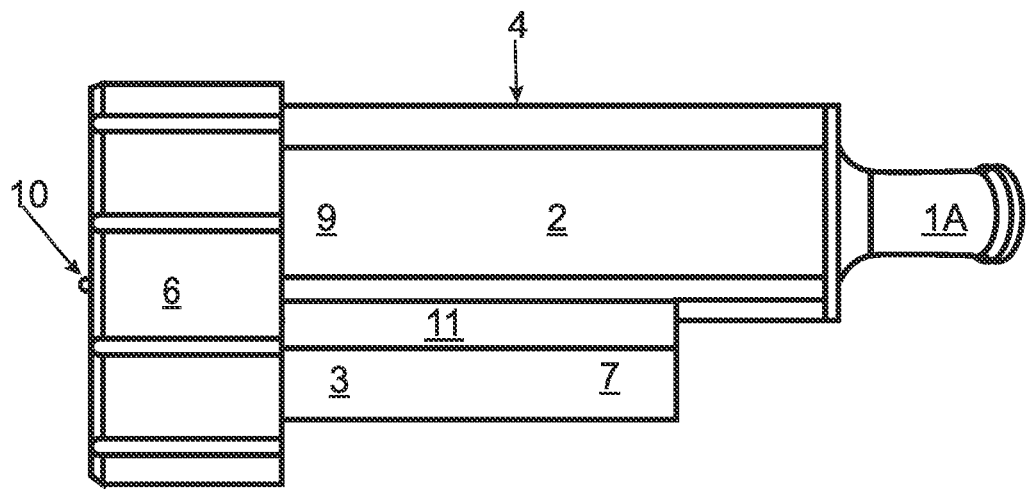
FIG. 1 is a side elevation of a hand-held breathing device of the invention.
Figure 2:
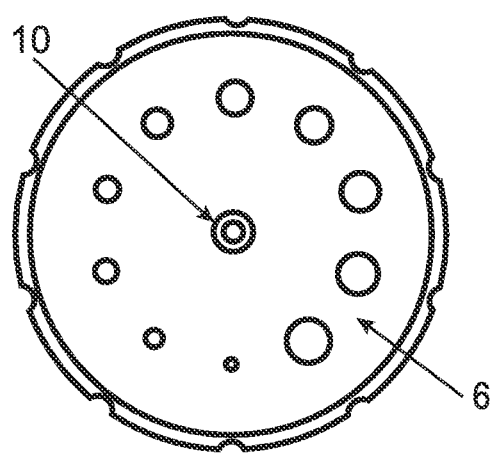
FIG. 2 is a elevation of an air outlet end of the device of FIG. 1.
Figure 3:
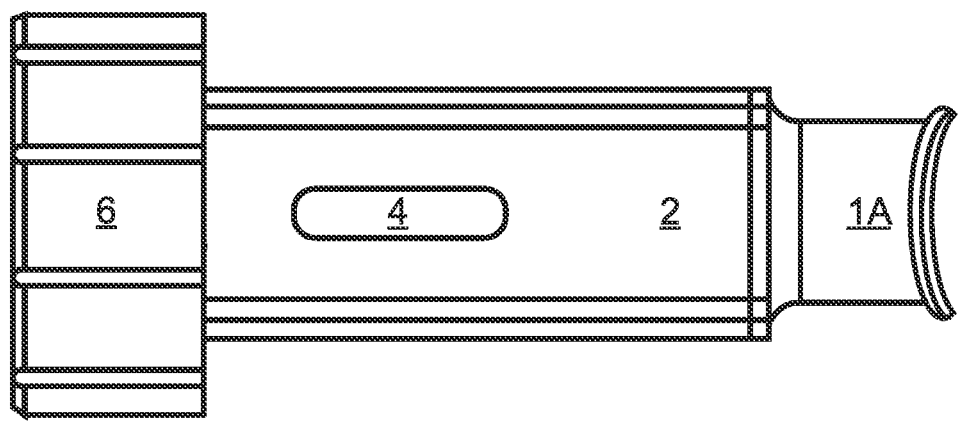
FIG. 3 is a top view of the device of FIG. 1.
Figure 4:
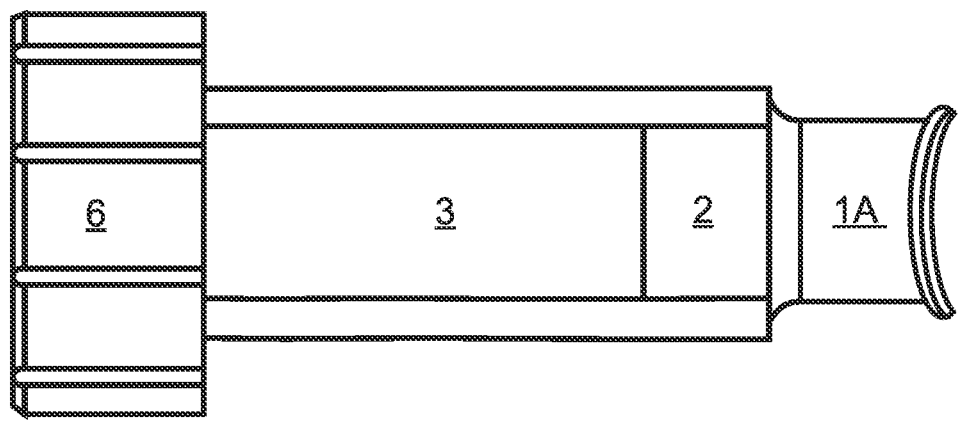
FIG. 4 is a bottom view of the device of FIG. 1.
Figure 5:
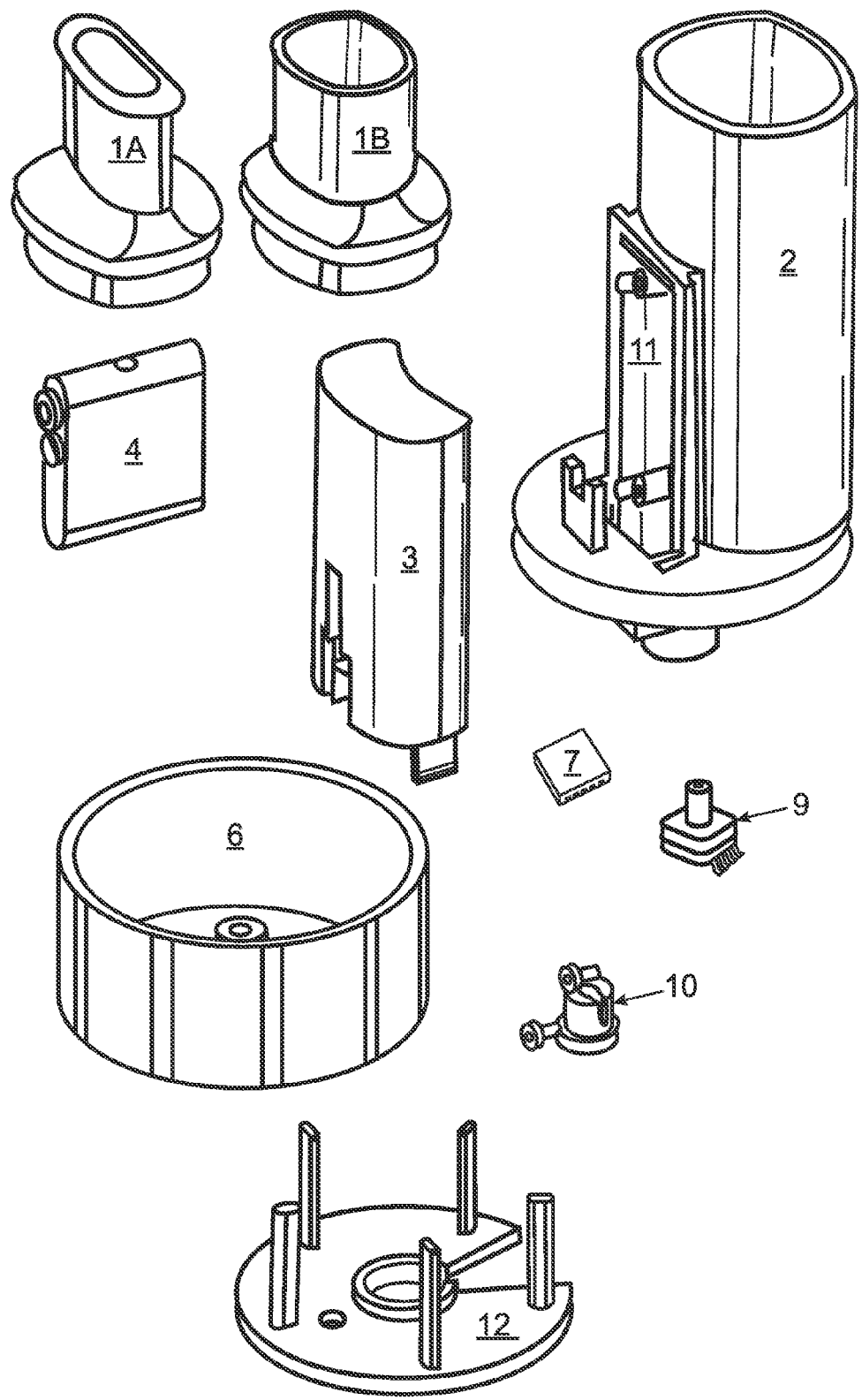
FIG. 5 is a an exploded view showing the principal components of the device of FIG. 1.
Figure 6D:
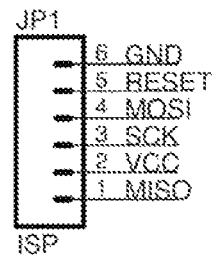
Figure 7:
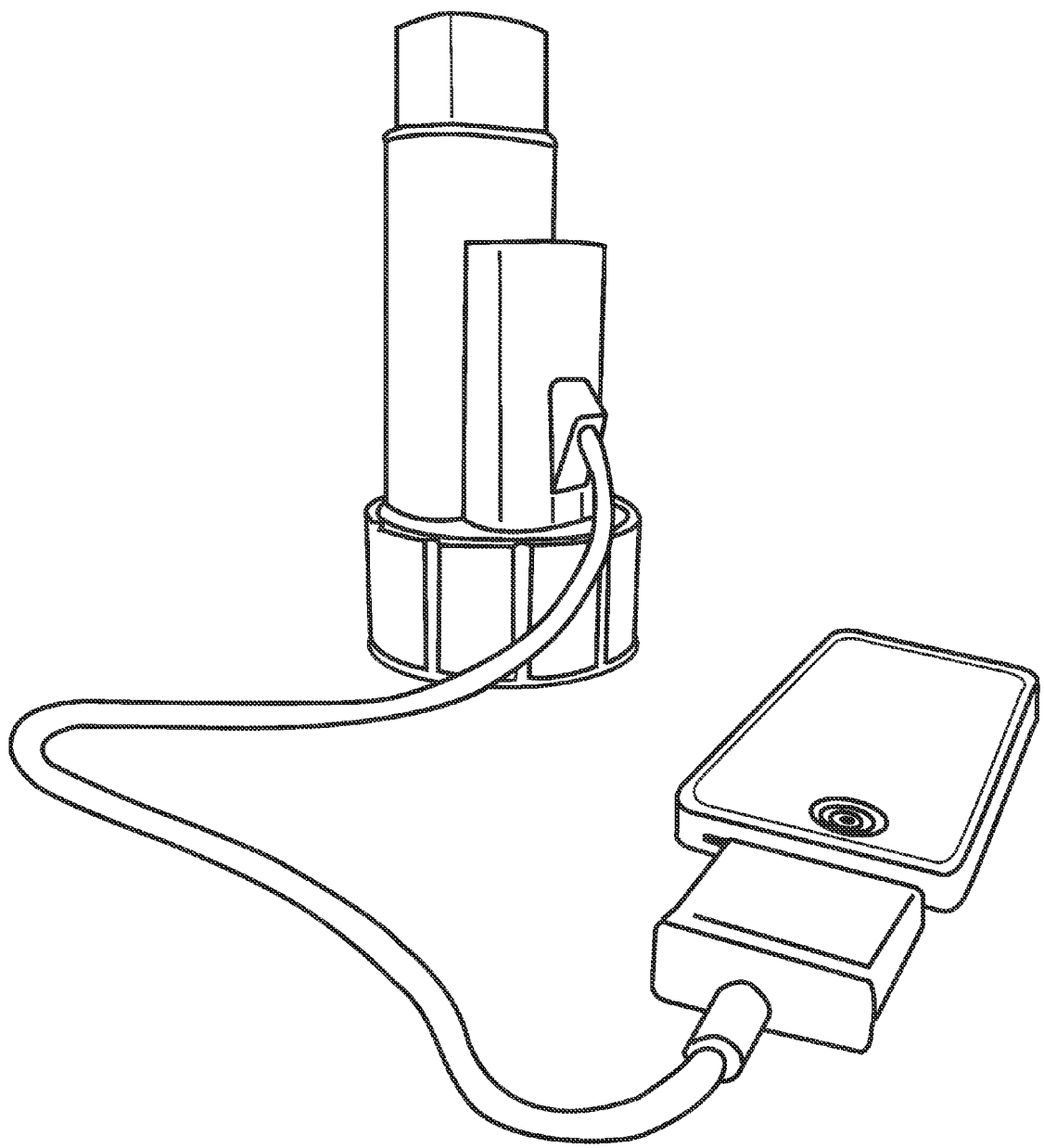
Figure 8:
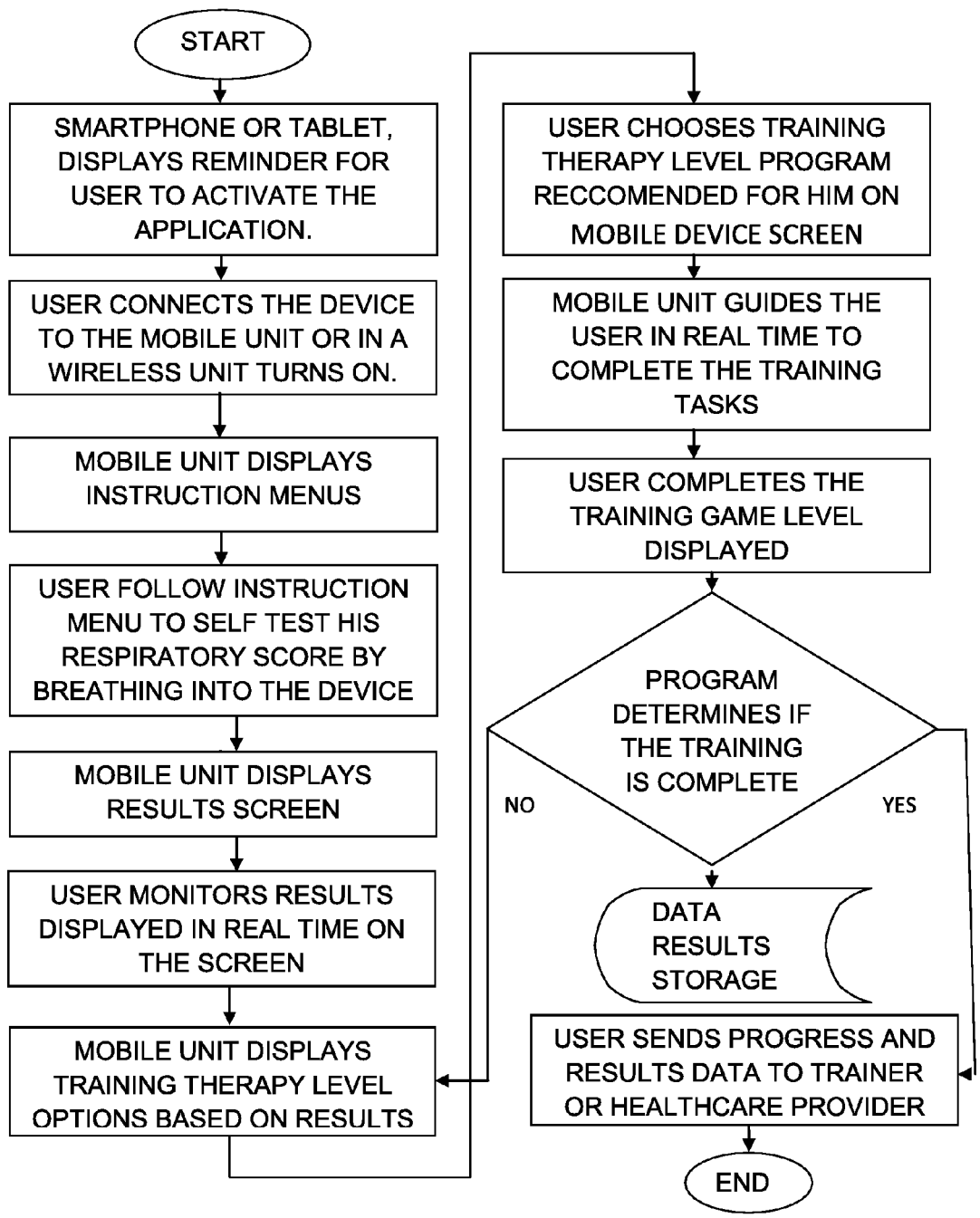
Figure 11:
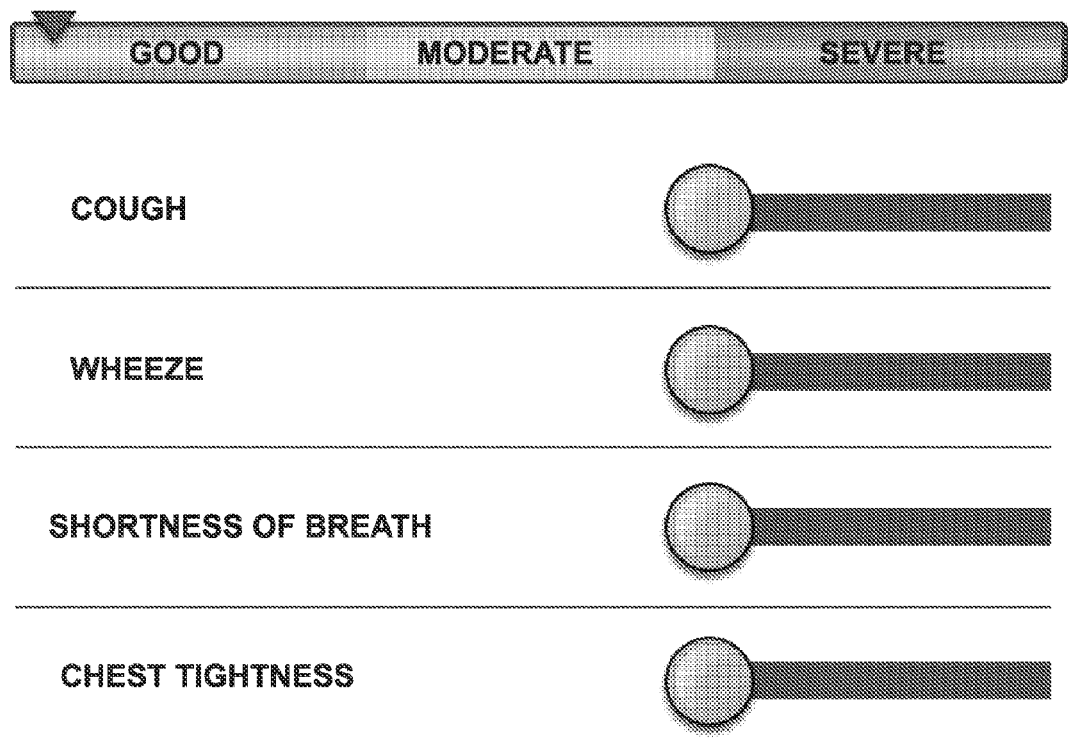
Figure 12:
Figure 13:
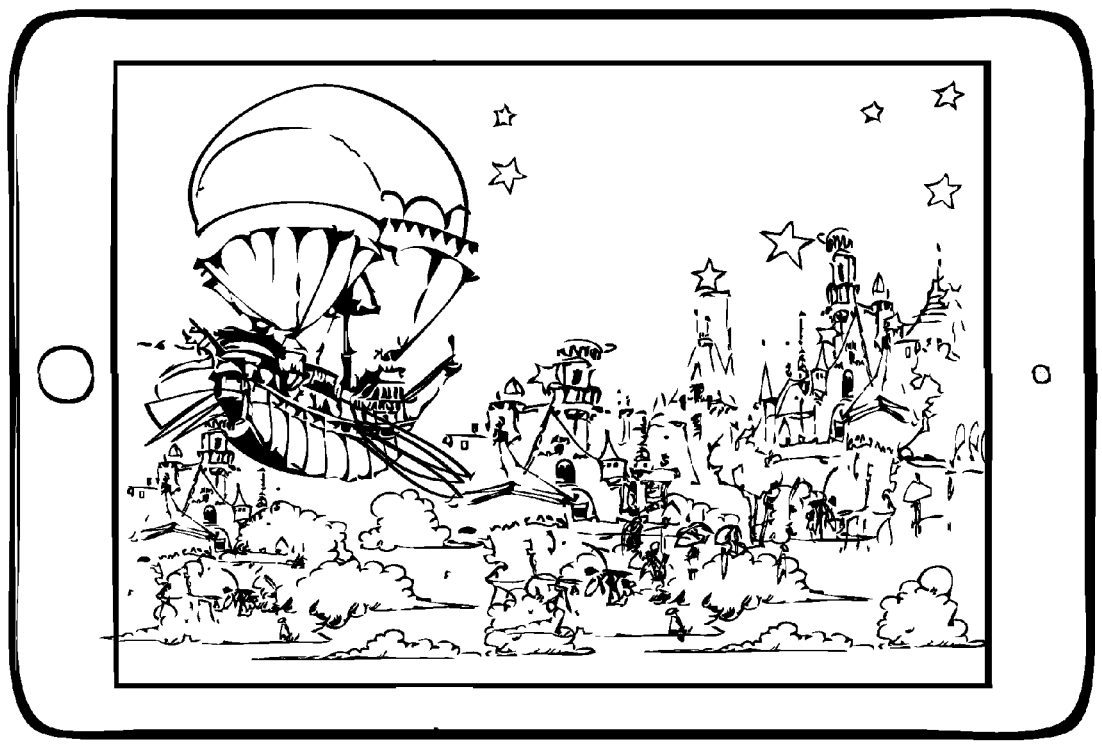
Figure 14:
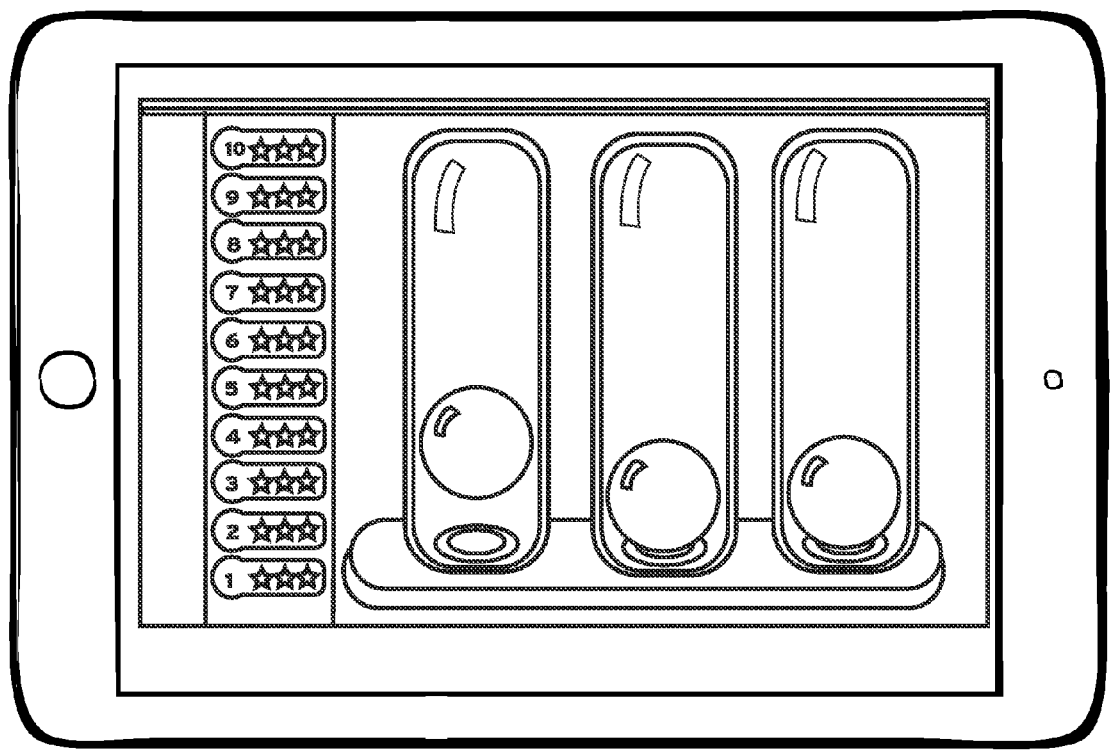

FIGS. 6A; 6B; 6C; 6D; 6E; and 6F are schematics of the voltage regulator; remote iPhone cable connector contact array; microprocessor/controller; output contact array; FDTI basic contact array;

FIG. 7 is a schematic view showing the breathing device connected to an iPhone;

FIG. 8 is a flow diagram of operational steps of a training routine according to the invention;

FIG. 9 is a screen shot of self test instructions and results for testing a user's peak expiratory flow;

FIG. 10 is a screen shot of self test instructions and results for testing a user's peak inspiratory flow;

FIG. 11 is a screen shot of a composite score (good, moderate or severe) of user's condition based on positions of input sliders moved by the user to indicate the subjective degree of any/all deleterious condition (s);

FIG. 12 is a screen shot depicting a sea diver;

FIG. 13 is a screen shot depicting an airship floating over terrain;

FIG. 14 is a screen shot simulation of an incentive spirometer.

Figure 17:
Figure 15:
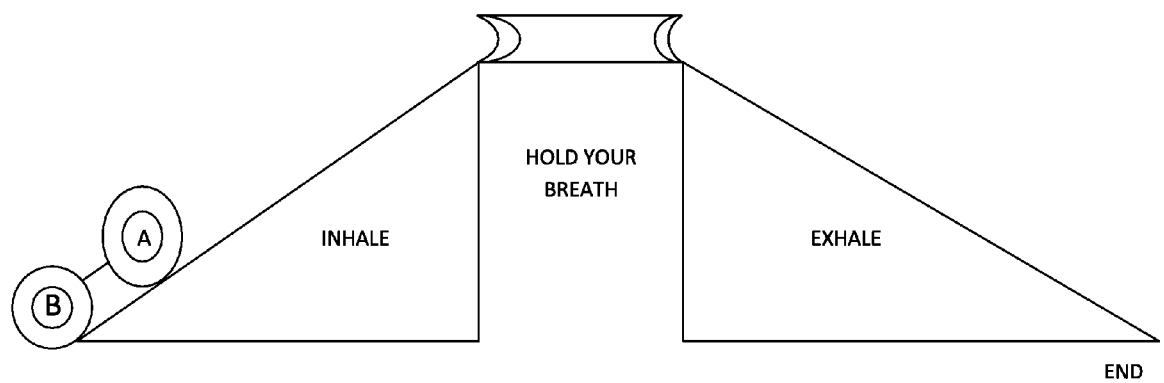
Figure 16:
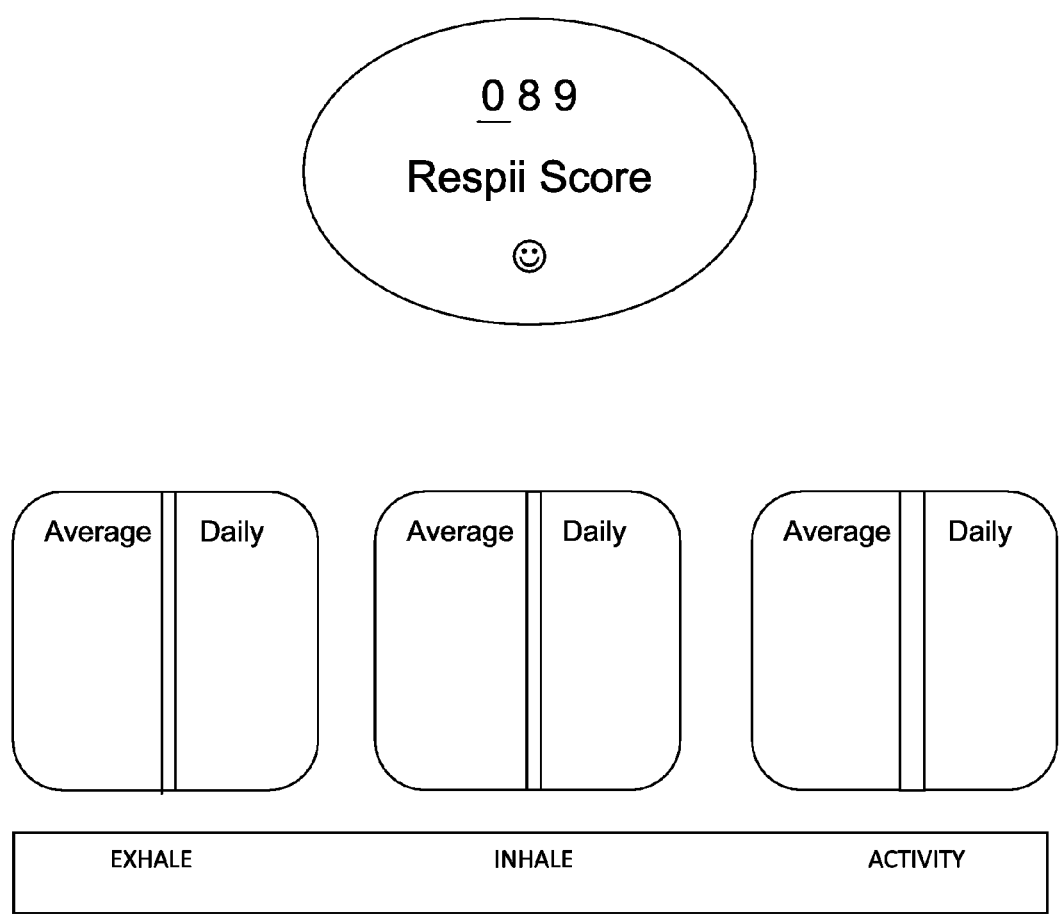

FIG. 15 is a screen shot depicting a 'follow the ball' game of a breathing/respiration training routine;

FIG. 16 is a screen shot of the user's cumulative score; and,

FIG. 17 is a screen shot of a menu of options for the user to select a self-test or a preferred game training routine.

PARTICULAR DESCRIPTION

As shown particularly in FIGS. 1-5, and 7, the hand-held breathing device/monitor comprises, alternative mouthpieces 1A and 1B, selectively (1A) removably mounted on one axial end of a tubular airflow or breathing chamber 2, and an air valve 6 mounted on the other end comprising an outer disc-form valve plate formed with a circular array of air ports of successively increasing size and a rotatable finger piece by which the outer valve plate can be manually rotated to bring selected outer ports of respectively different selected size into alignment with an air port on an inner, fixed valve plate 12 to adjust resistance to air flow and, thereby, breathing resistance, the position being registered on rotary DIP switch 10. A cap 3 covers a circuit board 11. An LED module 4 is mounted on the top of the chamber, in the sight of the user. The requisite air pressure sensor 9 and an accelerometer 7 to detect activity are also operably mounted in the housing at locations indicated.

The principal circuit components include voltage regulator 660 (FIG. 6A); Atmel ATMAGA328 8 bit microcontroller 680 (FIG. 6C), circuit 600 (FIG. 6E) of pressure sensor 9, circuit 650 (FIG. 6F) of 10 position rotary dip switch 10 and the connector to an iPhone 670 (FIG. 6B).

Pressure sensor MP3H6115ACBU is a free-scale semiconductor sensor that measures the air pressure in the chamber during exhaling and inhaling. As the temperature of air in the chamber can change by blowing in air at body temperature to the chamber, it is a high temperature accuracy integrated silicon pressure sensor for measuring absolute pressure with on-chip signal conditioning. The chosen pressure sensor is temperature compensated and calibrated Freescale's MP3H6115A series sensor integrates on-chip, bipolar operational amplifier circuitry and thin film resistor networks to provide a high output signal and temperature compensation.

The small form factor and high reliability of on-chip integration make the Freescale pressure sensor a logical and economical choice for this device. The MP3H6115A series piezo-resistive transducer is a state-of-the-art, monolithic, signal conditioned, silicon pressure sensor. This sensor combines advanced micromachining techniques, thin film metalization, and bipolar semiconductor processing to provide an accurate, high level analog output signal that is proportional to applied pressure.

The pressure operating range is 15 to 115 kPa, which covers the range of pressure we expect, using a 3V battery.

Figure 6E:
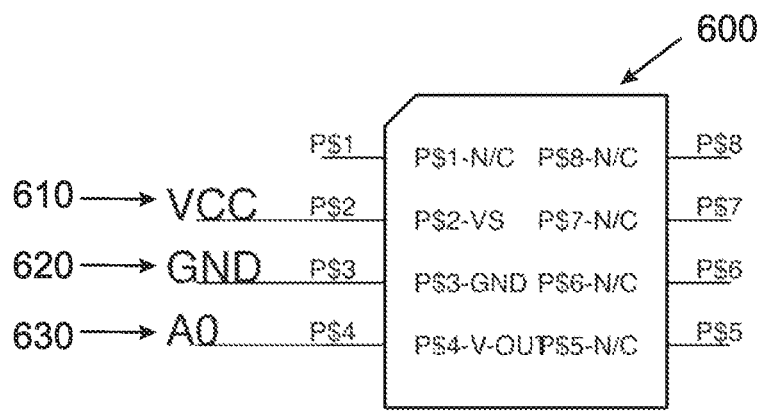
Figure 6F:
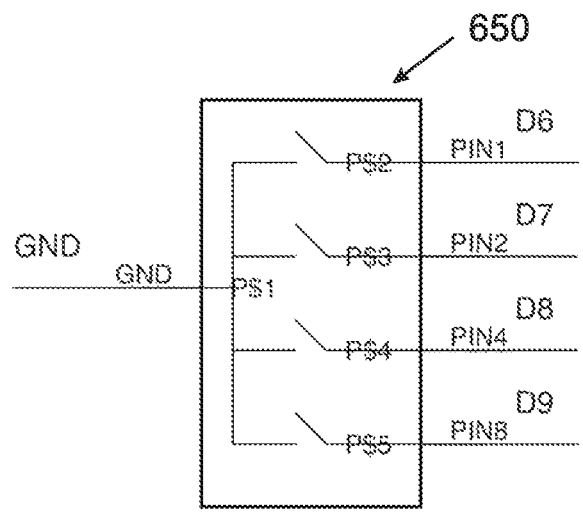

As can be seen in FIG. 6E, the sensor has only 3 useful connections: VCC—610, ground connection 620 and, the output signal connection 630. This is connected to the ADC0 pin in the MCU circuit in FIG. 6 below.

The 10 position dip switch FR01KC10H-S is mounted at the center of the rotary outer to record the user-selected port. The pressure sensor 600 and the 10 position dip switch 650 are the two inputs to the microcontroller 660 shown in FIG. 6C.

The voltage regulator 660 (FIG. 6A), 6, includes a MIC5205 Micrel chip. The MIC5205 is a 150 mA low noise LDO (Low Drop-Out) regulator made by Micrel, Inc., San Jose, Calif. 95131.

The MIC5205 is an efficient linear voltage regulator with ultra low-noise output, very low drop out and very low ground current. The MIC5205 offers better than 1% initial accuracy. It has been chosen to provide maximal stability to the pressure sensor measurements in this hand-held, battery-powered device. It obtains power from the iPhone 670 connector, designated as RAW. Its output is designated as VCC 692, also shown in the FIG. 6C. The connector 670 to an iPhone is used both for receiving power through RAW pin as well as performing the rs-232 serial communication with the MCU 680.

Microcontroller 680, process the signal from pressure sensor 600 and the control signal from the 10 position dip switch 650. The high-performance Atmel 8-bit AVR RISC-based microcontroller ATMEGA328 combines 32 KB ISP flash memory with read-while-write capabilities, 1 KB EEPROM, 2 KB SRAM, 23 general purpose I/O lines, 32 general purpose working registers, three flexible timer/counters with compare modes, internal and external interrupts, serial programmable USART, a byte-oriented 2-wire serial interface, SPI serial port, 8-channel 10-bit A/D converter in TQFP package, programmable watchdog timer with internal oscillator, and five software selectable power saving modes. The device operates between 1.8-5.5 volts so it is suited for the 3V of our device.

The pressure sensor 600 is connected to the 10 bit ADC PC0 (ADC0) channel as depicted in FIG. 6 below. This signal is processed by the MCU 680.

The digital serial communication output is sent through pin PC6 to the connector 670 of the iPhone as DTR designated as 690 (Data Terminal Ready (DTR) is a control signal in RS-232 serial communications.) Pin PC6 in MCU 680 also performs any needed manual reset when the RESET button is pressed. Pins PD0 and PD1 in MCU 680 perform the RX and TX (Receive and Transmit) needed for the serial communication with the iPhone through connector 670.

In addition to communicating with the iPhone App through connector 670, the MCU 680 utilizes an LED indicator that changes its illumination in proportion to changes in the pressure level.

Digital I/O pins are connected to the 10 position dip switch 650. By turning the 10 different diameters ports in the path of airflow, the user can change the level of air resistance for inhaling and exhaling, as required for the training. The changes in position are detected by the 10 position switch and transmitted through the digital I/O pins to the MCU 680.

Sequential steps of a typical training routine are shown in the flow chart of FIG. 8.

A smart phone or tablet computer etc on which the software is installed (or a cloud signal) displays a reminder for the user to activate the application. The user connects the breathing device to the mobile unit or switches on for wireless connection causing the mobile unit to display a menu offering a self-test or a preferred game routine to the user (FIG. 17). For a first time user the self-test option must be taken to establish a baseline performance following which combination self-test instructions and results screens (FIGS. 9 and 10) are displayed. The user follows the instructions by breathing into the device to self-test his respiratory performance and provide a resulting respiratory score which is displayed to him for monitoring in real time on the screen.

The mobile unit displays a menu of training therapy level options based on the test results and the user selects that preferred/recommended training option. The mobile displays instructions guiding the user in real time to complete the selected training routine. If the routine is completed, the results data is stored and the user transmits the results data to a trainer or health care provider. The screen shot of FIG. 11 shows a combination of an input screen and a result screen. The input is performed by the user between the inhale and exhale tests. The importance is that these results are being recorded with the numerical result numbers of the inhale and exhale testing exercises and are an additional data/parameter for creating the respiratory profile. Following up on these indicators is important for Asthma management.

In operation, the user slides one or more round symptom sliders appropriate to his subjective complaint to the right which advances the cursor on the top bar to the right, into a (green) zone on the left, yellow zone, middle and finally red, right side of the slider to indicate his cumulative, overall condition. Each movement of the symptom slider contributes incrementally to and affects the result of the overall condition and an accumulative symptom creates the GOOD, MODERATE OR SEVERE composite condition.

One can have bad cough but still be in a good condition but on the right side of good etc.

In the screen shots of FIGS. 12 and 13, the diver and balloon characters/icons rise and descend in real time in response the user's respiratory performance, as do the balls and score of incentive spirometer of FIG. 14.

The screen shot of FIG. 15 shows a game form training routine depicting an initially uphill and subsequently downhill path, joined at a summit by a bridging path and, leading and following ball objects (joined by elastic thread) traveling along the path, motion of the following ball being determined by inhalation and exhalation, respectively, of the user at predetermined strengths and durations to make the objects maintain a constant separation while the leading object is moved by the software at an appropriate, rate predetermined for the training routine. The user must hold his breath for a predetermined period of time while the first object traverses a top of the incline. The training routine procedure is restarted if the objects collide or a predetermined separation of the objects is exceeded.

The screen shot of FIG. 16, shows an accumulative simple points system (Respii score—trade mark) (that the user can always access and view his achievements. The score is for every parameter such as inhaling and exhaling combining with amount of activity that he does on an accumulative weekly schedule. User daily activity is compared with his weekly average and is computed to give his Respii score.

The screen displays a "Smiley," if the user does well and a "Frowney" if his score is low.

The invention claimed is:

1. A software operated method for both breathing training and respiratory muscle training comprising the steps of:
providing a breathing chamber having a mouthpiece whereby a user can inhale and exhale air through the chamber;
automatically measuring pressure, time and direction of air breathed through the chamber;
automatically processing and displaying on a remote screen, a real-time interactive graphic representing such air pressure, time and direction;
automatically displaying from memory a test breathing routine to a user, measuring and displaying the test results and, subsequently determining and displaying, for user selection, at least one of a stored series of appropriate personal training routines of different difficulties on the screen in accordance with a test result, whereby the user can monitor personal breathing performance on a real time basis and perform personal training routines .

2. The method of claim 1 including displaying a plurality of appropriate optional personal training routines of different difficulties on the screen enabling a user to select a personally preferred routine.

3. The method of claim 2, including the step of altering resistance to air flow through the chamber and, consequently, breathing resistance.

4. The method of claim 3 wherein, the graphic depicts screen movement of an object away from a start position to a target position by an amount reflecting such pressure, time (endurance) and direction.

5. The method of claim 4 wherein, the movement of the object is in opposite directions during inhalation and exhalation, respectively.

6. The method of claim 5 wherein, the object is a recognizable character/icon to stimulate personal amusement of a user.

7. The method of claim 6 wherein, for incentive training, a predetermined target position for the object is displayed on the screen and the object falls back to the start position when the predetermined target is not reached by the breathing of the user.

8. The method of claim 7, wherein for incentive training, the graphic depicts an initially uphill and subsequently downhill path, joined at a summit by a bridging path and, leading and following objects traveling along the path, motion of the following object being determined by inhalation and exhalation, respectively, of the user at predetermined strengths and durations to make the objects maintain a constant separation with the leading object which is moved by the software at an appropriate, predetermined rate for the training routine and, the user to hold his breath for a predetermined period of time while the first object traverses a top of the incline, the training routine procedure being restarted if the objects collide or a predetermined separation of the objects is exceeded.

9. A system for both breathing training and respiratory muscle training comprising a hand-held breathing device and training software;
   the breathing device comprising a chamber having an air port and a separate mouthpiece whereby a user can inhale and exhale through the chamber;
   an air pressure sensor in the chamber for providing an electrical signal signifying the direction and pressure of the air breathed through the chamber and,
   one of cable and wireless means for outputting such signal to a remote computing device or cloud, installed with the software, to automatically process and display a real-time interactive graphic representing such air pressure, time and direction and appropriate training routines on a remote screen;
   whereby the user can monitor personal breathing performance on a real time basis and perform the training routines.

10. The system of claim 9 including means for automatically displaying a plurality of appropriate optional personal training routines of different difficulties on the screen enabling a user to select a personally preferred routine.

11. The system of claim 10 including means for altering resistance to air flow through the chamber and, consequently, breathing resistance.

* * * * *